United States Patent [19]
Ziegler

[11] Patent Number: 5,249,028
[45] Date of Patent: Sep. 28, 1993

[54] GRAPHITE TUBE FURNACE

[75] Inventor: Fritz Ziegler, Bermatingen, Fed. Rep. of Germany

[73] Assignee: Fritz Ziegler Feinwerktechnik GmbH, Bermatingen, Fed. Rep. of Germany

[21] Appl. No.: 900,134

[22] Filed: Jun. 18, 1992

[30] Foreign Application Priority Data

Jun. 18, 1991 [DE] Fed. Rep. of Germany ....... 4120028

[51] Int. Cl.$^5$ ................................. G01N 21/74
[52] U.S. Cl. ........................ 356/312; 356/244
[58] Field of Search .................... 356/312, 244

[56] References Cited

U.S. PATENT DOCUMENTS 4,111,563 9/1978 Tamm ................. 356/312
4,657,389 4/1987 Littlejohn ............. 356/312

FOREIGN PATENT DOCUMENTS 381948 8/1990 European Pat. Off. ......... 356/312

Primary Examiner—F. L. Evans
Attorney, Agent, or Firm—Spencer, Frank & Schneider

[57] ABSTRACT

A graphite tube furnace for the electrothermal atomization of specimens for atomic absorption spectroscopy is proposed, which consists of an outer furnace body and an internal inner body. In order to avoid a premature atomization of the specimen, the inner body is designed as a cylindrical tube which is concentrically disposed in the furnace body and which is integrally connected to the furnace body via a single upper, end-face connecting web.

10 Claims, 2 Drawing Sheets

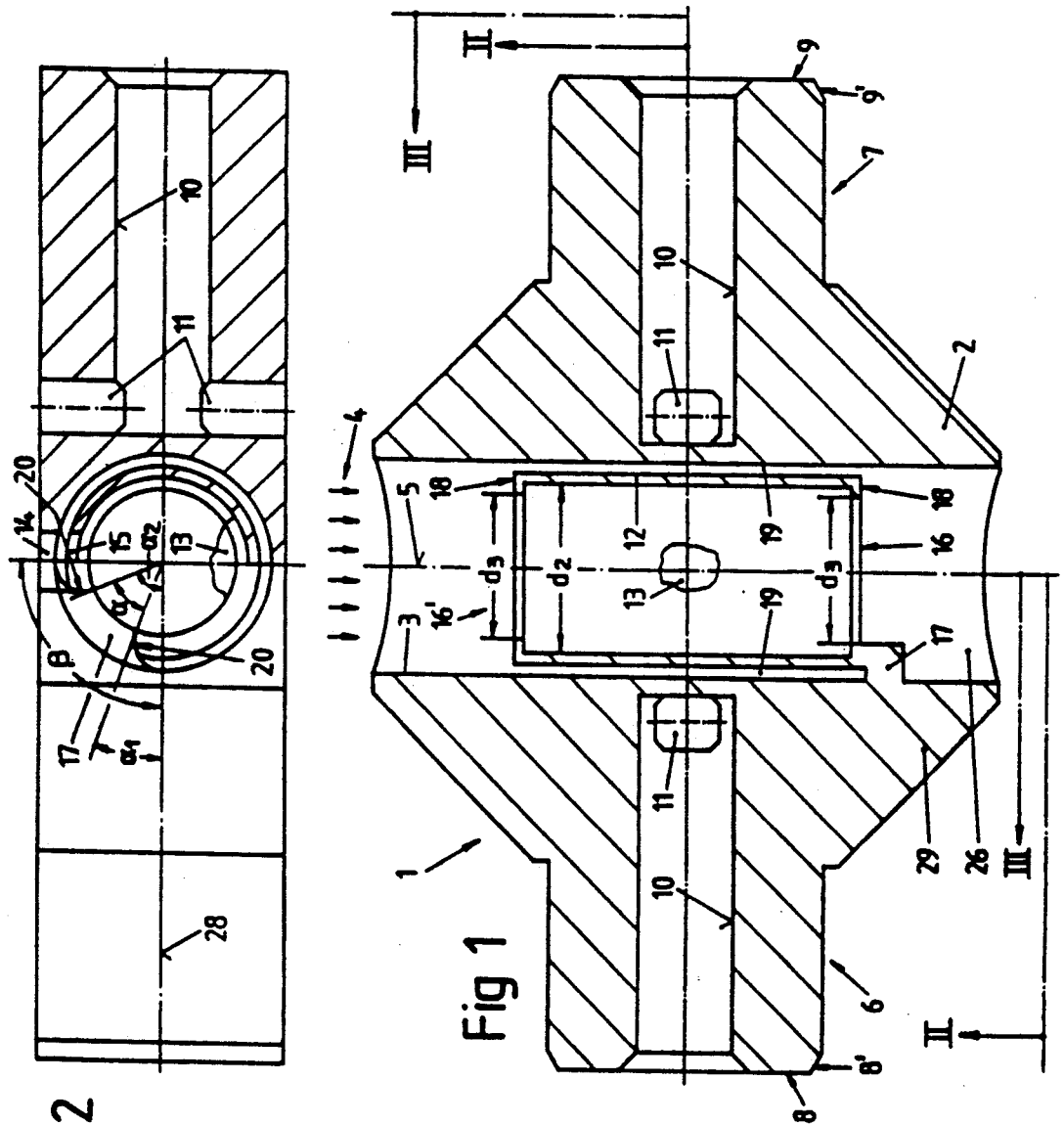

GRAPHITE TUBE FURNACE

BACKGROUND OF THE INVENTION

The invention relates to a graphite tube furnace for the electrothermal atomization of specimens for atomic absorption spectroscopy.

The known analysis of substances by means of atomic absorption spectroscopy is based on the recognition that any atom can absorb light of that wave form in which it itself also emits radiation. Consequently, the specimen to be analyzed, which is present in liquid or solid form, must be atomized in order to remove the atoms from a molecular association. By means of a hollow cathode lamp or the like, spectral lines are emitted which radiatively penetrate the atomic cloud of the specimen. As a result of absorption of specific spectral lines by specific atoms, the intensity of the spectral lines is attenuated. A spectral breakdown of the light in the monochromator separates out the resonance lines and displays their attenuation due to the absorption. The measure of the attenuation is a measure of the extent of the absorption and thus a measure for the presence of the quantity or of the concentration of the element under investigation in a specimen.

To atomize the specimen, the so-called graphite tube technique has become known, in which a high current flows longitudinally or transversely through a graphite tube furnace and thus the furnace is heated to a high temperature, e.g. a temperature as high as 3000° C. In this case, the hollow graphite cylinder is radiatively penetrated by the light beam of the hollow cathode lamp. By way of example, 5 to 100 microliters of substance are introduced through a small aperture onto a specimen platform in the graphite tube and are heated. In this case, the graphite tube is circumcirculated by an eg. argon gas current, in order to keep the oxygen of the air away and to prevent a combustion of the graphite.

Further technical details together with further literature references are indicated in EP 0,381,948 A1, columns 1 to 4. To explain the present invention, express reference is made to this prior art.

In the aforementioned literature reference, it is pointed out that the specimen to be analyzed is in general fed onto a so-called L'vov platform. This platform—also referred to hereinbelow as the specimen take-up or specimen store—is either a separate workpiece (see, for example, DE-U1 87/13,503) or a bearing element which is also integrated into the tube when the graphite tube furnace is produced.

The treatment of the specimen which is pipetted onto the inner specimen take-up, takes place in a first drying step for concentration and in a subsequent pyrolysis step to atomize the specimen. In this case, the graphite tube furnace is heated from room temperature to over 2000° C. in slightly more than one second; this takes place by very high currents within the graphite tube furnace. These high temperatures are maintained constant for a period of approximately 10 s, in order to achieve the required steps. After this, the graphite tube furnace is cooled down again to room temperature.

For the correct treatment of the specimen within these time intervals, it has already been stated in the aforementioned publication EP 0,381,948 that it is necessary to undertake a controlled heating of the graphite tube furnace and to avoid a premature atomization of the specimen. Accordingly, the heating process, the drying process and the subsequent atomization process should proceed with very great precision in terms of time, in order that, especially for the atomization process, a strong absorption signal should be obtained. In order to achieve this, according to the aforementioned publication it was proposed that the specimen take-up, having the shape of a semicylindrical shell, is connected as an inner body only at one end with the outer tube, so that on the one hand no current flows through said specimen take-up and thus it is not additionally heated. On the other hand, the intention is to avoid to a large extent a conduction of heat from the tubular furnace body through which current flows, to the specimen take-up via the connecting web. The heating of the specimen is to take place as far as possible exclusively by radiant energy via the tubular furnace body.

Since the tubular furnace body is intensely heated directly by the passage of a high current, an intense radiation also becomes established, which acts directly on the specimen lying on the open specimen take-up. In this case, the radiant energy or radiant power given off to the specimen is proportional to the fourth power of the radiation temperature, i.e. the radiant power acts directly and lastingly on the specimen to be analyzed. Thus, the radiation acting directly on the specimen prevents an effective delay of the atomization of the specimen. Indeed, DE 2,554,950 C2 discloses a graphite tube for the atomization of specimens, in which tube the inner body is designed as a cylindrical tube to take up the specimen. This inner tube is, however, connected to the likewise tubular outer body by a plurality of longitudinally extending ribs, so that this inner body having the shape of a cylindrical shell, through which a current likewise flows, is subjected to an intense heating, which acts directly on the specimen by the giving-off of radiant energy.

SUMMARY OF THE INVENTION

ADVANTAGES OF THE INVENTION

As compared with the known comparable devices, the graphite tube furnace according to the invention has the advantage that a further improvement in the treatment of the specimens to be analyzed is achieved. In particular, the improved treatment concerns an even more controlled temporal coordination of the drying section for the concentration of the specimen and the subsequent atomization of the specimen to perform atomic absorption spectroscopy. In this case, the invention proceeds from the recognition that a direct irradiation of the specimen by the graphite tube furnace through which current flows is avoided in that the specimen is disposed within a cylindrical inner tube as specimen take-up, which inner tube itself does not have current flowing through it and accordingly is heated only on account of the radiation of the outer tubular outer body. In this case, the connection between inner tube and outer tube is disposed in such a manner that it is disposed as far away as possible from the specimen, so that also the heat conduction between outer tube and inner tube and thus to the specimen plays no more than a subordinate role. As compared with the known design—having the shape of a semi-cylindrical shell—of the inner specimen take-up for the specimen, a closed inner tube has the advantage that the inner body, on account of its higher mass, is heated later but not as a whole more slowly, ie. is heated with a delay, and screens off a direct radiation influence of the outer tube on the specimen. Furthermore, the tubular closed inner body causes an inclusion of the atomized substance and thus a higher concentration of the atomic cloud density. This gives a stronger measurement signal. Finally, in the case of a tubular inner body, the connecting web to the furnace body can be disposed at a position remote from the specimen; in this case, the "coldest" position of the furnace body is taken into consideration. An additional rim prevents an overflowing of the substance to the outer tube; this may lead to a "prepeak" as a result of a premature atomization.

As compared with the open shell form, the closed form of the tubular specimen take-up is also more stable, so that it can be designed with even thinner walls. Further, the constant gap between inner tube and outer tube can be maintained more precisely in the case of the tubular form of the inner tube. This gives a precisely defined heating of the inner tube by the radiation of the furnace body; in this case, no direct radiation acts on the specimen, but only the indirect radiation of the inner tube acts on the specimen.

The measures set forth in the subclaims represent further advantageous refinements and improvements to the graphite tube furnace indicated in claim 1.

BRIEF DESCRIPTION OF THE DRAWINGS

Further details of the invention are shown in the drawing and explained in greater detail with reference to the description which follows. In the drawing:

FIG. 1 shows a transversely heated graphite tube furnace in a longitudinal section with a cylindrical-tubular inner specimen and a current supply situated transversely to the spectral line axis, FIG. 2 shows a side elevation of the furnace in partial section along the section line II—II in FIG. 1, FIG. 3 shows a partial section of the representation according to FIG. 1 along the section line III—III.

DETAILED DESCRIPTION OF THE DRAWINGS

Figures 4, 5:
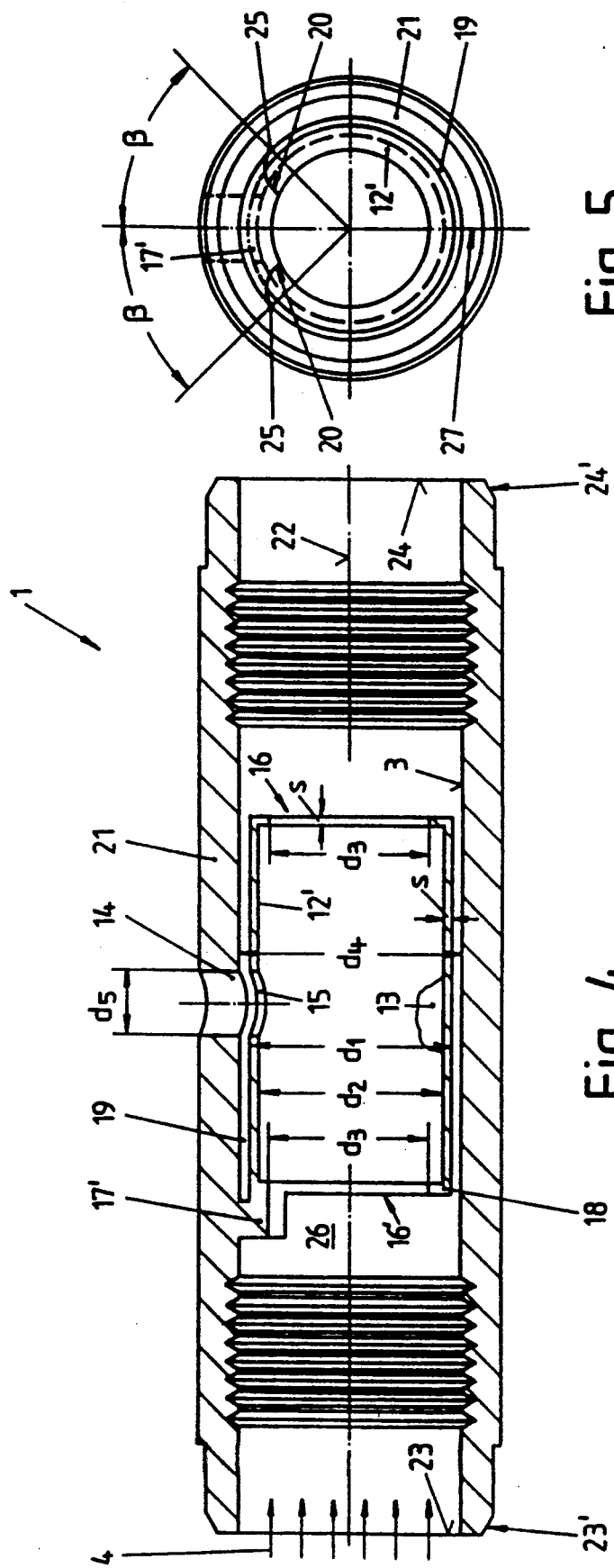
FIG. 4 shows an alternative construction of a graphite tube furnace with current supply in the longitudinal direction of the system.
FIG. 5 shows an end elevation of the representation according to FIG. 4.

The transversely heated graphite tube furnace 1 which is shown in FIGS. 1 to 3 in various elevations and sections, corresponds, in its basic construction, to the graphite tube furnace, shown in FIGS. 1 and 5 of EP 0,381,948, with an octagonal basic cross-section. Thus, express reference is made to the pertinent description of this known furnace.

As shown in FIG. 1, the transversely heated graphite tube furnace 1 consists of a furnace body 2 with an internal bore 3, which is penetrated by a measurement light beam for an atomic absorption spectrometer which is not shown in any greater detail. To heat the furnace body 2, two circular-cylindrical contact extensions 6, 7 are shaped perpendicular to the longitudinal axis 5 on the octagonal basic cross-section of the furnace body 2, the outer end surfaces 8, 9 of which contact extensions exhibit circulating contact chamfers 8', 9' which serve as connecting surfaces for a current passage through the graphite tube furnace. The contact extensions 6, 7 exhibit a central internal bore 10 with transverse axis 28 as well as branch channels 11 for the supply of protective gas in a manner known per se.

Within the furnace body 2 there is situated, concentrically with the longitudinal axis 5, a tubular inner body 12, which serves as platform or specimen take-up for a specimen 13 to be analyzed. The specimen 13 is fed via an outer insertion opening 14 in the furnace body 2 and an inner insertion opening 15 in alignment therewith, onto the specimentake-up of the inner body 12. The input of the specimen through these openings takes place, in general, using a micropipette.

According to the representation in FIGS. 1 and 2, the tubular inner body 12 is connected, in its upper, end-face end region 16 via a single, somewhat eccentrically disposed connecting web 17, with the outer furnace body 2. The connecting web 17, which extends as a narrow adjoining circular ring segment over an angle $\alpha$ 50° (FIG. 2), is shaped on at the rear end region 16 of the inner body 12 in such a manner that it is situated at the "coldest" position of the furnace body 2. As shown in FIG. 2, the connecting web 17 accordingly is not situated in the per se optimal uppermost position furthest removed from the specimen 13, but in a position, comparable with a clock dial, between the FIGS. 10 and 11, i.e. the angle $\alpha$ is between the angles $\alpha_1 \approx 20°$ and $\alpha_2 \approx 70°$ in relation to the transverse axis 28. In this region, the transversely heated furnace body exhibits its most intense accumulation of material (region 29 in FIG. 1), so that the "coldest" position of the furnace body 2 in the course of the heating process is situated here, on account of the greater mass and the associated delay in heating as well as of the lower ohmic resistance and the associated lower electrical heating.

Accordingly, the position of the connecting web 17 is disposed so that the latter is on the one hand as far distant as possible from the specimen 13, in order to obtain the lowest possible premature thermal influencing of the specimen 13 by thermal conduction effects. On the other hand, the connecting web 17 is set at such a position of the transversely heated furnace body 2 which is heated with a delay, on account of its greater accumulation of mass 29 and its lower ohmic resistance, i.e. at the "coldest" position of the furnace body 2. Accordingly, the connecting web 17 is disposed so as to be somewhat eccentrically offset. If appropriate, the furnace body 2 can exhibit, in the region of the connecting web 17, a corresponding "build-up of material". As a result of the aforementioned measures, a maximum delay in the heating curve of the specimen and an optimal specimen treatment are achieved. In this case, a flow of current through the specimen take-up itself and thus the additional heating thereof are avoided.

On account of the small spacing between specimen take-up 12 and furnace body 2 (approximately 0.3 mm), the desired rapid heating of the system by the thermal radiation is nevertheless assured.

According to the representation in FIG. 3, in a preferred illustrative embodiment the inner body 12 exhibits an external diameter $d_1 \approx 5.6$ mm and an internal diameter $d_2 \approx 5$ mm. This gives a wall thickness s for the inner body of $s \approx 0.3$ mm, i.e. the specimen take-up is designed to be very thin-walled. At its two end faces 16, 16', the inner body 12 is provided with a small circular-ring setoff or rim 18, which leaves a passage opening for the beam path 4 of $d_3 \approx 4$ mm. As a result of the rim 18, it is possible that even greater specimen quantities 13 may be taken up, without this resulting in the overflow of the specimen take-up. An overflow of the specimen may lead to a premature vaporization of the specimen and thus to an undesired measurement value as "prepeak". The internal diameter of the furnace body 2 is $d_4 \approx 6.15$ mm. The outer or inner input opening 14, 15 exhibits a diameter $d_5 \approx 1.6$ mm.

As is clearly illustrated in FIGS. 1 and 4, the inner body 12 is produced as a single unitary piece with the furnace body 2 from a solid. To this end, the required annular gap 19 is produced by means of a special tool between furnace body 2 and inner body 12, while maintaining a connecting web 17 having the shape of a circular segment. The connecting web 17 exhibits, at its two segment ends, transition radii 20 to the furnace body 2, which exhibit an order of magnitude of 0.75 mm.

The embodiment of the invention according to FIGS. 4 and 5 comprises a graphite tube furnace 1, a furnace body 21 of which has current flowing through it in the axial longitudinal direction, ie. in the direction of its longitudinal axis 22. This corresponds to a graphite tube arrangement as shown in DE 2,554,950 C2. To this end, the contact chamfers 23', 24' at the end faces 23, 24 of the furnace body 21 are designed as connecting faces for a current connection; this corresponds to the contact chamfers 8', 9' in FIG. 1. The inner body 12' for forming the specimen take-up for the specimen 13 is, in FIGS. 4 and 5, likewise designed as a tubular body, with a connecting web 17', which is connected, in the upper end region of the end face 16', integrally with the inner body 12'. As is evident from FIG. 5, this bonding-on to form the connecting web 17 is in this instance disposed so as to be symmetrical with respect to the vertical axis of symmetry 27, since in the case of this furnace body 21 no mass concentration such as is present in the illustrative embodiment according to FIG. 1 is present; in this case, the radius-type transitions 20 end, in their upper region, at a point 25 which is distant in an arc angle $\beta = 45°$ from the vertical axis of symmetry 27. This gives a very gradual transition from the inner body 12' to the furnace body 21; this contributes to the stability of the system. Between furnace body 21 and inner body 12' there is again provided an annular gap 19, which is produced by an appropriate incizing tool.

The dimensions $d_1$ to $d_4$ in FIG. 4 correspond to those as described in FIG. 3. The same applies to the diameter $d_5$ of the two input openings 14, 15. In principle, the arrangement of the inner body 12' as specimen take-up within the furnace body 21 in FIGS. 4 and 5 thus corresponds to that of the inner body 12 in the furnace body 2 according to FIG. 1. In so far as they correspond, identical parts are accordingly identified by identical reference symbols.

The invention is not restricted to the illustrative embodiment which has been described and shown. Rather, it also covers all further developments and refinements within the activity of a person skilled in the art, within the bounds of the inventive concept.

I claim:

1. A graphite tube furnace for the electro-thermal atomization of specimens for atomic absorption spectros-copy, having a furnace body, which is open at both of its ends and which is tubular and through which current flows in the transverse direction or the longitudinal direction and in the interior of which an inner body which can be heated by the furnace body is disposed as specimen take-up, said inner body being a circular-cylindrical tube, which is concentrically disposed within the furnace body, and a single narrow connecting web for connecting said inner body and said furnace body to each other, said web being connected to said inner body at an upper end-face end thereof.

2. The graphite tube furnace as claimed in claim 1, wherein the connecting web between inner body and furnace body is shaped on, integrally as a circular-segment transition, in the upper region of an end face of the inner body.

3. The graphite tube furnace as claimed in claim 1, wherein the connecting web merges, by a transition radius, tangentially into the inner wall of the furnace body.

4. The graphite tube furnace as claimed in claim 1, wherein the inner body exhibits a wall thickness s of approximately 0.3 mm, with a spacing from the inner wall of the furnace body of approximately 0.3 mm.

5. The graphite tube furnace as claimed in claim 1, wherein the specimen take-up exhibits, at its two end faces, a circular-ring setoff.

6. The graphite tube furnace as claimed in claim 1, wherein the specimen take-up and the furnace body are produced as one unitary piece.

7. The graphite tube furnace as claimed in claim 1, wherein the connecting web is designed to be so thin that it exhibits the lowest possible thermal conductivity.

8. The graphite tube furnace as claimed in claim 1, wherein in the case of a transversely heated furnace body the connecting web between tubular specimen take-up and furnace body is disposed in such a manner that it is situated at the "coldest" position of the furnace body, the "coldest" position exhibiting a greater accumulation of material of the furnace body and/or a lower ohmic resistance.

9. The graphite tube furnace as claimed in claim 1, wherein in the case of a longitudinally heated furnace body the connecting web between inner tube and furnace body is disposed with axial symmetry at the upper, end-face end.

10. The graphite tube furnace as claimed in claim 1, wherein the furnace exhibits, in the region of the connecting web, an accumulation of material and a lower ohmic resistance to produce a "colder" position.

* * * * *